US012682991B2

(12) United States Patent
Larmuseau

(10) Patent No.: US 12,682,991 B2
(45) Date of Patent: Jul. 14, 2026

(54) METHODS AND SYSTEMS FOR COMPRESSED FAST HEALTHCARE INTEROPERABILITY RESOURCE (FHIR) FILE SIMILARITY SEARCHING

(71) Applicant: KONINKLIJKE PHILIPS N.V., Eindhoven (NL)

(72) Inventor: Adriaan Joris H Larmuseau, West-Flanders (BE)

(73) Assignee: Koninklijke Philips N.V., Eindhoven (NL)

( * ) Notice: Subject to any disclaimer, the term of this patent is extended or adjusted under 35 U.S.C. 154(b) by 165 days.

(21) Appl. No.: 18/289,133

(22) PCT Filed: May 7, 2022

(86) PCT No.: PCT/EP2022/062385
§ 371 (c)(1),
(2) Date: Nov. 1, 2023

(87) PCT Pub. No.: WO2022/238277
PCT Pub. Date: Nov. 17, 2022

(65) Prior Publication Data
US 2024/0233890 A1 Jul. 11, 2024

(30) Foreign Application Priority Data
May 14, 2021 (CN) .......................... 202110528668.3

(51) Int. Cl.
*G06F 17/00* (2019.01)
*G06F 16/14* (2019.01)
(Continued)

(52) U.S. Cl.
CPC ........... *G16H 10/60* (2018.01); *G06F 16/152* (2019.01); *G06F 16/1744* (2019.01)

(58) Field of Classification Search
CPC .. G16H 10/60; G16H 10/152; G16H 10/1744; G16H 10/907; G16H 10/148;
(Continued)

(56) References Cited

U.S. PATENT DOCUMENTS 10,216,754 B1 * 2/2019 Douglis .............. G06F 16/1744
12,183,439 B2 * 12/2024 Cano ...................... G16H 10/40
(Continued)

FOREIGN PATENT DOCUMENTS

WO 2020178724 A1 9/2020

OTHER PUBLICATIONS

International Search Report and Written Opinion from PCT/EP2022/062385 mailed Aug. 10, 2022.
(Continued)

*Primary Examiner* — Greta L Robinson

(57) ABSTRACT

A method (100) for generating a compressed Fast Healthcare Interoperability Resources (FHIR) file using a file compression system (200), comprising: (i) receiving (104) an uncompressed FHIR file; (ii) extracting (106), from the uncompressed file, a predetermined plurality of different resource types: (iii) generating (108), from the extracted predetermined plurality of different resource types, a fixed-length FHIR patient profile fingerprint, wherein the fixed-length FHIR patient profile fingerprint comprises a fixed-length floating point value feature vector, the fixed-length floating point value feature vector comprising a predetermined plurality of sub-feature vectors each representing a different extracted resource type, and wherein each sub-feature vector comprises a plurality of elements of the respective extracted resource type; (iv) compressing (110), using a trained compression algorithm, the generated fixed-length FHIR patient profile fingerprint to generate a com-
(Continued)

pressed FHIR fingerprint; and (v) storing (112) the compressed FHIR fingerprint in a database.

13 Claims, 4 Drawing Sheets

(51) Int. Cl.
 *G06F 16/174*   (2019.01)
 *G16H 10/60*   (2018.01)
(58) Field of Classification Search
 CPC .... G16H 10/13; H03M 7/3082; H03M 7/707;
                   G06F 21/6245
 See application file for complete search history.

(56)      References Cited

U.S. PATENT DOCUMENTS

| | | |
|---|---|---|
| 2016/0238486 A1 | 8/2016 | Bense et al. |
| 2020/0257657 A1* | 8/2020 | Ertl .......................... G06F 7/582 |
| 2021/0019556 A1* | 1/2021 | Ganguly ........... G06F 18/24137 |
| 2021/0056136 A1 | 2/2021 | Cano Ceron et al. |
| 2021/0098080 A1 | 4/2021 | Wuerstle et al. |
| 2021/0124777 A1* | 4/2021 | Oztaskent .............. G06V 20/46 |

OTHER PUBLICATIONS

Anis Sharafoddini et al: "Patient Similarity in Prediction Models Based on Health Data: A Scoping Review", JMIR Medical Informatics,vol. 5, No. 1, Mar. 3, 2017 (Mar. 3, 2017), pp. 1-18, XP055482088, DOI: 10.2196/medinform.6730 p. 1-p. 2.

Grahame Grieve: "Resources For Health: A Fresh Look Proposal< Health Intersections Pty Ltd", Aug. 18, 2011 (Aug. 18, 2011), XP055949021, Retrieved from the Internet: URL:http://www.healthintersections.com.au/?p=502[retrieved on Aug. 4, 2022].

Wang A: "An Industrial-Strength Audio Search Algorithm", Proceedings of 4th International Conference on Music Information Retrieval, Baltimore, Maryland, USA, Oct. 27, 2003 (Oct. 27, 2003).

Zhu et al "Measuring Patient Similarities via a Deep Architecture with Medical Concept Embedding" 2016 IEEE 16th Int. Conf. on Data Mining, Dec. 12, 2016, p. 749-758.

* cited by examiner

400

METHODS AND SYSTEMS FOR COMPRESSED FAST HEALTHCARE INTEROPERABILITY RESOURCE (FHIR) FILE SIMILARITY SEARCHING

CROSS REFERENCE TO RELATED APPLICATIONS

This application is a U.S. national phase application of International Application No. PCT/EP2022/062385 filed on May 7, 2022, which claims the benefit of CN application Serial No. 202110528668.3 filed on May 14, 2021 and are incorporated herein by reference.

FIELD OF THE DISCLOSURE

The present disclosure is directed generally to methods and systems for generating and utilizing compressed Fast Healthcare Interoperability Resource (FHIR) files.

BACKGROUND

Many medical and research applications of medical data require similarity searching. Finding patients and/or treatments with similar features can provide insight into patient trajectory, forecast, and/or prediction, patient treatment, and much more. Thus, identifying similar patients can have a huge benefit on patient healthcare outcomes.

One concern associated with similarity searching of medical data in a medical database is that searching for similar patients can require the transmission or communication of privacy sensitive medical information. This transmission of sensitive information can be a regulatory issue as well as a privacy and/or security risk.

One solution for safe similarity searching of medical data is the searching of data while it is still encrypted. Thus, current methods explore the use of methods such as homomorphic encryption which enables analysis of data while it is encrypted. However, homomorphic solutions are severely limited in the amount of data they can process. As such, even the best solutions remain too limited for real world use.

Many electronic health record systems utilize the Fast Healthcare Interoperability Resource (FHIR) format, created by the Health Level Seven International (HL7) healthcare standards organization, to store and communicate medical data. FHIR is a standard that describes data formats and elements (i.e., resources) as well as an API for exchanging electronic health records. However, FHIR files can be very large files and thus similarity searching using FHIR files can be an onerous process.

SUMMARY OF THE DISCLOSURE

Accordingly, there is a continued need in the art for methods and systems that enable quick and efficient similarity searching of FHIR files. There is further a continued need in the art for methods and systems that enable searching of homomorphic encrypted FHIR files to ensure privacy and security of those files.

The present disclosure is directed to inventive methods and systems for similarity searching of FHIR data such as patient profiles. Various embodiments and implementations herein are directed to a method and system configured for generating and utilizing highly-compressed FHIR files. According to an embodiment, the highly-compressed FHIR files may be utilized for homomorphic searching, among many other searching techniques. A file compression system receives one or more uncompressed FHIR files. The system extracts, from one or more of the received files, a plurality of different resource types found within the file. The number and types of resources extracted from the file can be predetermined by the system or a user. The file compression system then generates a fixed-length FHIR patient profile fingerprint from the extracted plurality of resource types. According to an embodiment, the fixed-length FHIR patient profile fingerprint comprises a fixed-length floating point value feature vector. The fixed-length floating point value feature vector, in turn, comprises a predetermined plurality of sub-feature vectors each representing a different extracted resource type, and each sub-feature vector comprises a plurality of elements of the respective extracted resource type. The file compression system compresses the generated fixed-length FHIR patient profile fingerprint using a trained compression algorithm of the system, thereby generating a compressed FHIR fingerprint. The compressed FHIR fingerprint can then be stored in a database and utilized for fast and efficient similarity search.

Generally, in one aspect, a method for generating a compressed Fast Healthcare Interoperability Resources (FHIR) file using a file compression system is provided. The method includes: (i) receiving an uncompressed file, the uncompressed file configured as a FHIR file; (ii) extracting, from the uncompressed file, a predetermined plurality of different resource types; (iii) generating, from the extracted predetermined plurality of different resource types, a fixed-length FHIR patient profile fingerprint, wherein the fixed-length FHIR patient profile fingerprint comprises a fixed-length floating point value feature vector, the fixed-length floating point value feature vector comprising a predetermined plurality of sub-feature vectors each representing a different extracted resource type, and wherein each sub-feature vector comprises a plurality of elements of the respective extracted resource type; (iv) compressing, using a trained compression algorithm, the generated fixed-length FHIR patient profile fingerprint to generate a compressed FHIR fingerprint; and (v) storing the compressed FHIR fingerprint in a database.

According to an embodiment, the fixed-length floating point value feature vector comprises six sub-feature vectors.

According to an embodiment, the compressed FHIR fingerprint comprises a fixed-length bit vector.

According to an embodiment, the trained compression algorithm comprises an iterative quantization approach. According to an embodiment, the iterative quantization approach generates a locality-sensitive hashing function configured to generate the fixed-length bit vector from the generated fixed-length FHIR patient profile fingerprint.

According to an embodiment, the method further includes the step of training the trained compression algorithm, comprising: (i) receiving a plurality of FHIR files; (ii) processing the received plurality of FHIR files; (iii) training the compression algorithm to generate a locality-sensitive hashing function; and (iv) storing the generated locality-sensitive hashing function. According to an embodiment, processing the received plurality of FHIR files comprises: (i) labeling one or more similarities between the received plurality of FHIR files; and/or (ii) altering one or more of the received plurality of FHIR files to generate an altered FHIR file.

According to an embodiment, the method further includes searching for similarity to one or more of the compressed FHIR fingerprints stored in the database.

According to an embodiment, the method further includes reporting a result of the step of searching for similarity to one or more of the compressed FHIR fingerprints stored in the database.

According to another aspect is a system configured to generate a compressed Fast Healthcare Interoperability Resources (FHIR) file. The system includes: an electronic medical record database comprising a plurality of uncompressed files, each of the uncompressed files configured as a FHIR file; a locality-sensitive hashing function configured to generate a fixed-length bit vector from a generated fixed-length FHIR patient profile fingerprint; and a processor configured to: (i) extract, from each of the plurality of uncompressed files, a predetermined plurality of different resource types; (ii) generate, from the extracted predetermined plurality of different resource types, a fixed-length FHIR patient profile fingerprint, wherein the fixed-length FHIR patient profile fingerprint comprises a fixed-length floating point value feature vector, the fixed-length floating point value feature vector comprising a predetermined plurality of sub-feature vectors each representing a different extracted resource type, and wherein each sub-feature vector comprises a plurality of elements of the respective extracted resource type; (iii) compress, using the locality-sensitive hashing function, the generated fixed-length FHIR patient profile fingerprint to generate a compressed FHIR fingerprint; and (iv) store the compressed FHIR fingerprint in a database.

According to an embodiment, the processor is further configured to search for similarity to one or more of the compressed FHIR fingerprints stored in the database. According to an embodiment, the system further comprises a user interface, and the processor is further configured to report, via the user interface, a result of searching for similarity to one or more of the compressed FHIR fingerprints stored in the database.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. The figures showing features and ways of implementing various embodiments and are not to be construed as being limiting to other possible embodiments falling within the scope of the attached claims. Also, the drawings are not necessarily to scale, emphasis instead generally being placed upon illustrating the principles of the various embodiments.

DETAILED DESCRIPTION OF EMBODIMENTS

Figure 1:
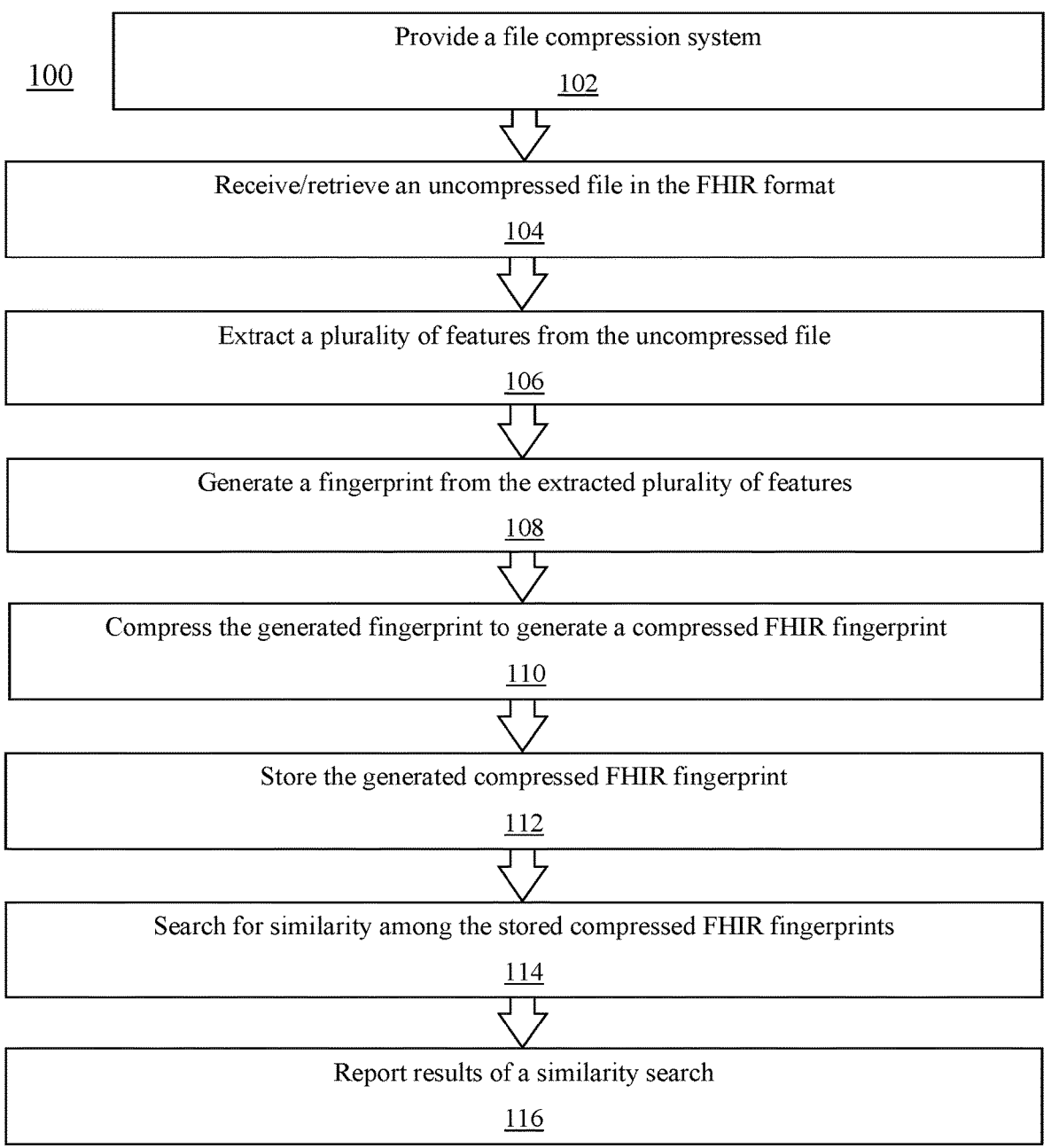
FIG. 1 is a flowchart of a method for generating highly-compressed FHIR files, in accordance with an embodiment.

The present disclosure describes various embodiments of a system and method configured to enable searching of homomorphic encrypted FHIR files to ensure privacy and security of those files. More generally, Applicant has recognized and appreciated that it would be beneficial to provide a method and system to generate and utilize highly-compressed FHIR files using a file compression system. The file compression system receives one or more uncompressed FHIR files. The system extracts, from one or more of the received files, a plurality of different resource types found within the file. The number and types of resources extracted from the file can be predetermined by the system or a user. The file compression system then generates a fixed-length FHIR patient profile fingerprint from the extracted plurality of resource types. According to an embodiment, the fixed-length FHIR patient profile fingerprint comprises a fixed-length floating point value feature vector. The fixed-length floating point value feature vector, in turn, comprises a predetermined plurality of sub-feature vectors each representing a different extracted resource type, and each sub-feature vector comprises a plurality of elements of the respective extracted resource type. The file compression system compresses the generated fixed-length FHIR patient profile fingerprint using a trained compression algorithm of the system, thereby generating a compressed FHIR fingerprint. The compressed FHIR fingerprint can then be stored in a database and utilized for fast and efficient similarity search.

In certain embodiments, researchers and/or healthcare professionals may utilize healthcare or research systems to rapidly find highly similar FHIR patient resources by means of a novel locality sensitive hashing solution. One continuing challenge for handling real-world data and finding similar FHIR profiles is the size of the data. The methods and systems described or otherwise envisioned herein create fingerprint of FHIR files. The multi-faceted fingerprint is constructed in a manner that intelligently discriminates against those elements of FHIR files that do not contribute to uniqueness. In addition, the methods and systems described or otherwise envisioned herein obtain a small final fingerprint by utilizing a novel iterative quantization approach to produce a special-purpose locality sensitive hash (LSH) function.

In addition to solving the data size issues encountered by the homomorphic encryption of real world data, the methods and systems described or otherwise envisioned herein provide additional positive effects. For example, the derived similarity preserving compressions offer a highly performant solution for detecting duplicate (FHIR) records, and enduring problem that consumers face. In general, duplicate detection has either been imprecise or very slow due to the large size and complexity of FHIR files. However, the novel compression methods and systems described or otherwise envisioned herein can identify the most highly likely duplication candidates within milliseconds.

Thus, according to an embodiment, the methods and systems described or otherwise envisioned herein comprise a fingerprint scheme configured to reduce a FHIR file into a multi-vector feature vector scheme that preserves the similarity properties of the FHIR file. In addition, the method and systems comprise an iterative quantization approach to further reduce the feature vector into small easily searchable bit vectors. This is useful both for general FHIR based similarity search as well as homomorphic encryption solutions where data size has exponential performance impact.

The embodiments and implementations disclosed or otherwise envisioned herein can be utilized with any system utilizing or otherwise comprising the FHIR standard, including but not limited to medical devices or systems. For example, one application of the embodiments and implementations herein is to improve medical monitoring systems such as, e.g., a Philips® Patient Monitoring system such as the Philips IntelliSpace® Precision Medicine products (manufactured by Koninklijke Philips, N.V.), among many other products. However, the disclosure is not limited to these devices or systems, and thus disclosure and embodiments disclosed herein can encompass any device or system utilizing or otherwise comprising FHIR.

Referring to FIG. 1, in one embodiment, is a flowchart of a method 100 for generating and utilizing highly-compressed FHIR files using a file compression system. The methods described in connection with the figures are provided as examples only, and shall be understood not to limit the scope of the disclosure. The file compression system can be any of the systems described or otherwise envisioned herein. The file compression system can be a single system or multiple different systems.

Figure 2:
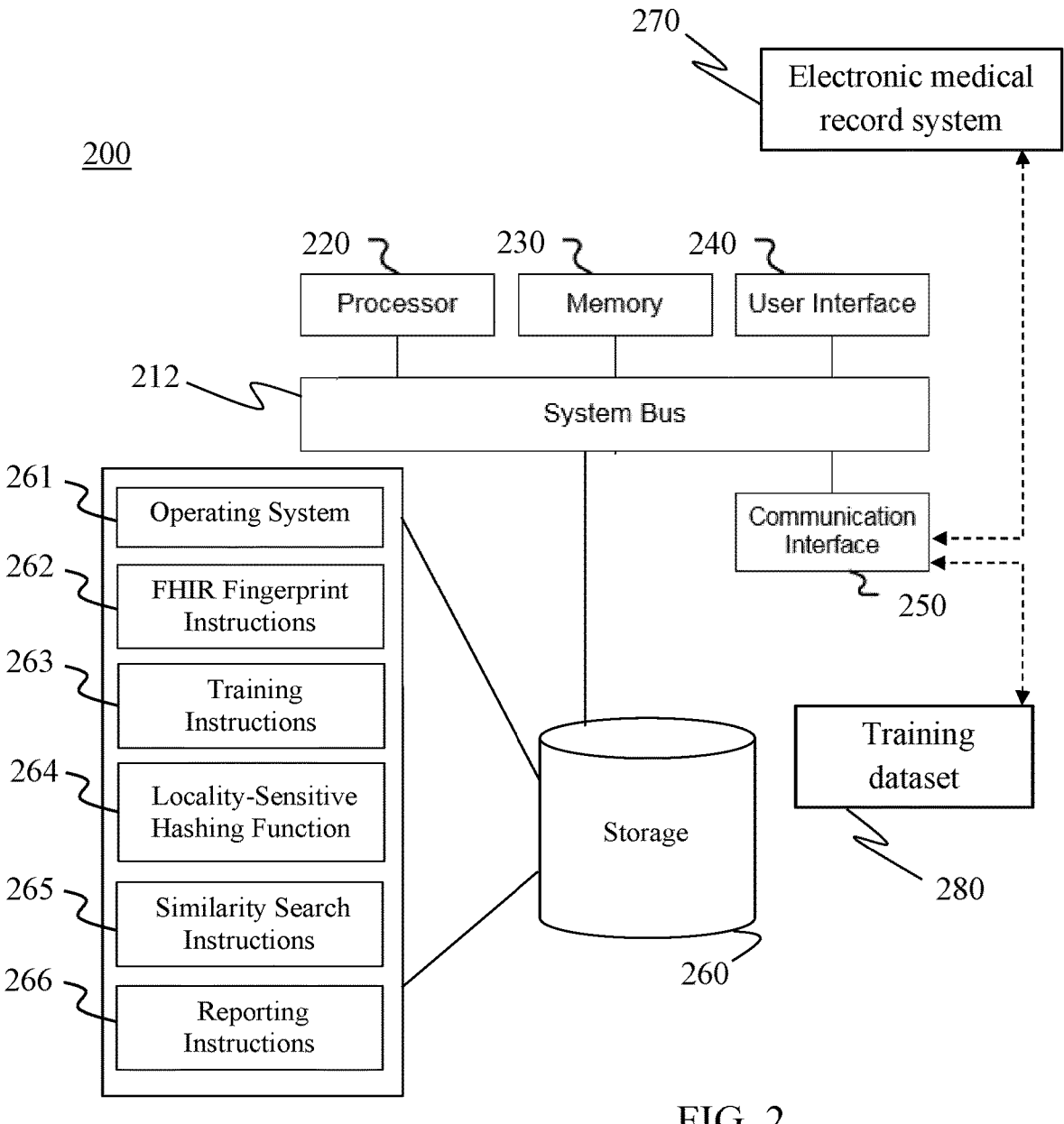
FIG. 2 is a schematic representation of a FHIR file compression system, in accordance with an embodiment.

At step 102 of the method, a file compression system 200 is provided. Referring to an embodiment of a file compression system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, file compression system 200 can be any of the systems described or otherwise envisioned herein. Other elements and components of system 200 are disclosed and/or envisioned elsewhere herein.

At step 104 of the method, the file compression system receives an uncompressed file. According to an embodiment, the uncompressed file is configured, organized, or otherwise comprising a FHIR format. The uncompressed file can be any file, document, or other structure comprising data organized, structured, or otherwise formatted according to the FHIR standard. According to an embodiment, the uncompressed file comprises medical data about a patient. The medical data or information can be any medical data or information capable of being stored, formatted, or otherwise configured according to the FHIR standard.

According to an embodiment, the file is received and/or requested from a database of files, such as an electronic medical record database or system 270. The electronic medical record database or system may be any local or remote database or system. For example, the file compression system may be a component of an electronic medical record database or system. Thus, the file compression system may be configured to access uncompressed files in the electronic medical record database or system, compress the file as described or otherwise envisioned herein, and store or otherwise provide the compressed file back in or to the electronic medical record database or system. As another example, the file compression system may be an intermediary between two systems and configured to compress files before communicating the file from one system to a second system. For example, the file compression system may be configured to receive one or more uncompressed files from an electronic medical record database or system to another system, including but not limited to a second medical database or system.

At step 106 of the method, according to an embodiment, the file compression system extracts or otherwise accesses, retrieves, or utilizes a predetermined plurality of different resource types from the uncompressed file. The resources can be any resource type utilized or defined by the FHIR standard. A resource can comprise one or more structured data items as described by the definition of the resource type.

According to an embodiment, the plurality of different resource types can be predetermined or selected by a user or the system. The selection can be based, in whole or in part, for example, on a desired outcome or use of the file compression system or the output of the file compression system. For example, if the compressed file will be utilized for similarity searching for a specific purpose, that specific purpose may define the different resource types selected. Alternatively, the resource types may be selected as to enable broad possibilities for similarity searching, storage, and/or other utilization of the compressed, stored FHIR file.

Figure 4:
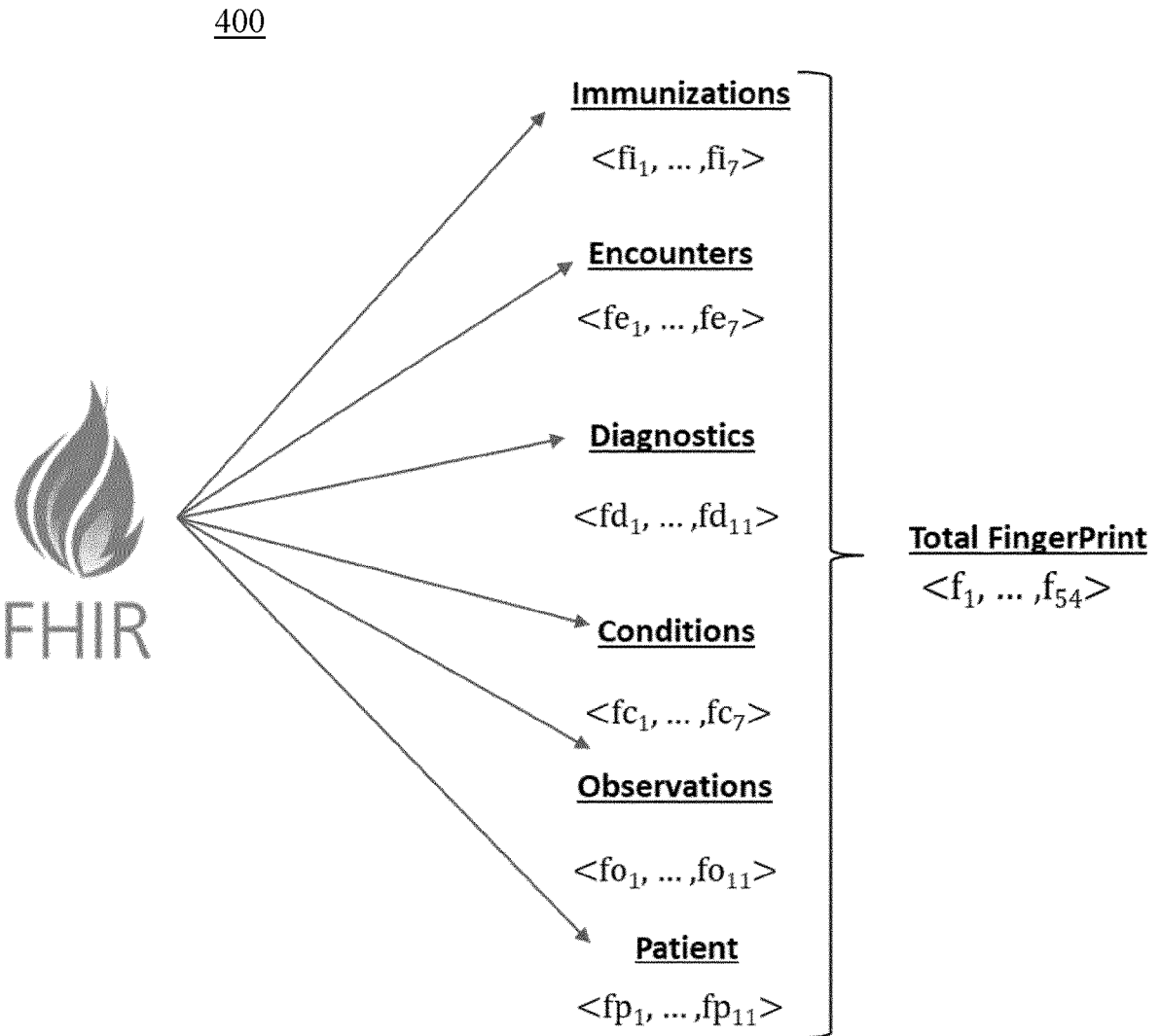
FIG. 4 is a flowchart of a method for processing a FHIR file, in accordance with an embodiment.

For example, referring to FIG. 4, in accordance with just one possible embodiment of a file compression system, a plurality of different resource types and associated data items are utilized or extracted from a FHIR file. Pursuant to this non-limiting example, six different resource types are extracted from or utilized from the received or obtained FHIR file: (i) Immunizations; (ii) Encounters; (iii) Diagnostics; (iv) Conditions; (v) Observations; and (vi) Patient. The file compression system may comprise some or none of these resource types, and may comprise fewer or many more than the resource types selected for this particular non-limiting example.

According to an embodiment, each respective resource type is associated with a predetermined or variable number of associated structured data items for that respective resource type: (i) Immunizations (7 data items); (ii) Encounters (7 data items); (iii) Diagnostics (11 data items); (iv) Conditions (7 data items); (v) Observations (11 data items); and (vi) Patient (11 data items). This results in a total of 54 data items. The file compression system may comprise some or none of these resource types and associated data items, and may comprise fewer or many more than the resource types and/or data items selected for this particular non-limiting example.

According to an embodiment, extraction of the plurality of different resource, and the one or more structured data items associated with each resource, can be accomplished by a variety of embodiments for resource and data item identification, extraction, and/or processing, including any method for extracting features from a dataset. The outcome of a feature processing step or module of the file compression system is a set of patient features related to medical information about a patient. This extracted or processed data can be utilized in subsequent steps of the method. The extracted or processed data can be utilized immediately or can be stored in local or remote storage for subsequent use.

At step 108 of the method, according to an embodiment, the file compression system generates a fixed-length FHIR patient profile fingerprint using the extracted predetermined plurality of different resource types and associated data items. According to an embodiment, the fixed-length FHIR patient profile fingerprint comprises a fixed-length floating point value feature vector. According to an embodiment, the fixed-length floating point value feature vector includes a predetermined plurality of sub-feature vectors each repre-
senting one of the predetermined and selected different
extracted resource types. According to an embodiment, each
sub-feature vector comprises a plurality of elements, such as
the extracted associated data items, associated with the
respective extracted resource type.

The length of the fixed-length FHIR patient profile fin-
gerprint can be predetermined by a user or by the system.
The length may be dependent upon, for example, the dif-
ferent resource types selected by or otherwise utilized by the
file compression system. For example, as more resource
types are utilized, the length of the fingerprint may get
longer.

Referring again to FIG. 4, in accordance with just one
possible embodiment of a file compression system, six
different resource types are extracted from or utilized from
the received or obtained FHIR file, with associated struc-
tured data items for that respective resource type: (i) Immu-
nizations (7 data items); (ii) Encounters (7 data items); (iii)
Diagnostics (11 data items); (iv) Conditions (7 data items);
(v) Observations (11 data items); and (vi) Patient (11 data
items). This results in a total of 54 data items. Accordingly,
the FHIR patient profile fingerprint is a 54 floating point
value feature vector for the FHIR file. This feature vector is
a combination of six sub-feature vectors each capturing a
separate resource type of the FHIR patient profile. As can be
noted in the figure each feature vector has a different length,
in this example some are seven elements long and others are
eleven elements long. To obtain these lengths, the following
algorithm was utilized, although many other approaches are
possible:

```
For i in [2, 3, 5, 7, 11, 13, . . .]
    S = For x in SampleSet:
```

$$ALG_3(x[resourcetype], i)\ Q = \frac{\sum_{s \in S}\left(\frac{\sum_{r \in S\setminus\{s\}} \vartheta(r, s)}{|S| - 1}\right)}{|S|}$$

```
    If Q < D:
        Return i
```

According to an embodiment, the logic in this algorithm
is as follows. Given a resourcetype from the six selected
FHIR resource types and a large representative sampleset of
FHIR files one tries to find the optimal prime number size i
of the feature vector by, for each candidate prime number,
first deriving a set of fingerprints for all files in the sampleset
by means of algorithm three (described in detail below) of
that size i. Next, the average correlation between the
samples in fingerprinted set Q is computed using the Spear-
man Correlation metric θ. If Q falls below some minimum
threshold D (in our embodiment D=0.55) then the prime
number i chosen as the length.

According to an embodiment, novel algorithm three (de-
scribed in detail below) is utilized to derive the fixed-length
FHIR patient profile fingerprint. However, to facilitate the
underpinnings of the development and use of novel algo-
rithm three, the following textual similarity algorithm (i.e.,
algorithm two) is described:

```
                Given i,
                resourcety
                pe result =
                [0₁...0ᵢ]
                For r in resourcetype
```

8

-continued

```
                For k,v in r
                    v1 = WMC(k)
                    If v is Number:
                        v2 = ME(v)
                    Else:
                        v2 = WMC(v)
                    result += v1+v2
                Return normalize (result)
```

According to an embodiment, this basic fingerprinting
formula works by breaking down the key value pairs that
make up the FHIR json files into feature vector encodings
that are summed and then add the end normalized. The
feature vector encoding of strings is done by means of a
weighted Markov chain WMC of the integer values of the
characters of the string. This encoding is a decay encoding,
lowering the weight of each subsequent character. The
feature vector encoding of numbers deconstructs each num-
ber into a mantissa and exponent ME, encoding them
separately into the feature vector.

However, according to an embodiment of the file com-
pression system, algorithm three (described in detail below)
is utilized to encode the fingerprints into feature vectors of
the derived optimal size, rather than algorithm two described
above. While algorithm two is an effective tool for deter-
mining brute force correlation between records, when deriv-
ing the actual fingerprints the file compression system
utilizes a more refined method that can maximize correlation
between FHIR for their most significant values, ignoring the
correlations in structure as the structure is a fixed property
of FHIR. Another way to state this is that the system doesn't
utilize the actual correlation of the underlying textual rep-
resentation of the FHIR record, the system correlates records
based on their most significant aspects. For example, if two
patients both comprise frequent check-ups, utilizing algo-
rithm two will increase their overall correlation or similarity.
However, for most purposes this type of similarity (i.e.,
frequent check-ups) is not very useful, as patients may
utilize or attend frequent health check-ups for very different
reasons. Conversely, if one patient weighs 78.3 kilos and the
other patient weights 79.1 kilos, algorithm two will identify
this as a substantial dissimilarity. Algorithm three generates
final fingerprints without these issues, thereby resulting in
much more precise similarities. Accordingly, novel algo-
rithm three greatly outperforms algorithm two. Algorithm
three is as follows:

```
        Given i, resourcetype, Freq, Sev,
        Bucket result = [0₁...0ᵢ]
        For r in resourcetype
            For k,v in r:
                Decay = 0
                If hasClass(k):
                    c = Class(k)
                    Decay = (Max((Freq(c) − 1),0))
                * (1−Sev(c)) If v is Number:
                    If v is Metric:
                        v1 = Bucket(v)
                    Else:
                        v1 = ME(v)
                Else:
                    v1 = WMC(v)
                v1 *= Decay result += v1
        Return normalize(result)
```

This algorithm adds three additional functions, namely
Freq, Sev, and Bucket. The Freq function produces a fre-
quency value for each class type, pre-computed from a sampleset of FHIR files. The Sev function computes the severity of the class, pre-defined manually. There are many ways to define or compute the severity of a class, and may depend at least in part on the needs of the user, the utilization of the file compression system, and other parameters. For example, simple check-ups may have a severity set at 0, while long-time in-patient hospitalization may have severity set very high at 0.9. The Bucket function distributes metric values into categories, similarly to how such data is de-identified.

According to one embodiment, in experiments algorithm two identified approximately 20% of randomly generated files as likely to be highly similar using the Spearman correlation. In contrast, algorithm three identified approximately 1% of randomly generated files as likely to be highly similar. Review of these randomly generated files indicated that approximately 1% of the files were indeed highly similar. Also according to experiments performed to review algorithms two and three, it was shown that algorithm three was able to identify approximately 98% of slightly altered duplicate files.

At step 110 of the method, a trained compression algorithm of the file compression system is utilized to compress the generated fixed-length FHIR patient profile fingerprint from step 108 of the method, to generate a compressed FHIR fingerprint. According to an embodiment, the system utilizes iterative quantization with automatically generated training data to produce a locality sensitive hash function. Many different approaches to the iterative quantization are possible.

The file compression system utilizes any algorithm for compression suitable for downstream similarity searching. According to just one embodiment, the file compression utilizes a library such as the LSHBOX C++ library. Although the system may utilize a FHIR-HAPI library, this is just one non-limiting example and there are other libraries and/or tools available to use. According to an embodiment the system compresses the FHIR fingerprints to bit vectors that are 20 bits long to support up to one million patients. However, the bit vector may be of any length, and thus may be shorter for small databases or longer for larger databases.

According to an embodiment, the file compression system generates a bit vector for each FHIR fingerprint. These bit vectors are ideal for finding highly similar and/or duplicate FHIR files. According to one example, the methods and systems described or otherwise envisioned herein might be utilized to enable quick and efficient discovery of patients with similar clinical pathways. According to an example, the system could adjust or otherwise alter the multi-vector to exclude the patient and/or encounter vectors and redo the iterative quantization step with this smaller feature vector.

According to an embodiment, the methods and systems described or otherwise envisioned herein generate a fixed-length FHIR patient profile fingerprint of 54 floating point numbers, although many other sizes are possible. The 54-point fingerprint comprises a data storage size of approximately 3 kb, which compares to an average FHIR patient profile size of approximately 700 kb, resulting in a compression factor of more than 200.

However, for homomorphic encryption in particular a file of 3 kb may still be far too large. Accordingly, the methods and systems described or otherwise envisioned herein apply iterative quantization to compress the 3 kb file to a much smaller size. According to just one embodiment, the iterative quantization compresses each 3 kb FHIR fingerprint file to a bit vector of 20 bits, although many other vector lengths are possible.

Iterative quantization derives a locality-sensitive hashing function for performing the compression in a similarity-preserving manner by training the algorithm using a large labeled dataset. According to an embodiment, the dataset and accompanying labels are produced from a set of unique FHIR files. The FHIR files are processed by labeling similarities between files discovered by measuring the Spearman correlation to the result of algorithm three, and by automatically generating slightly altered duplicates. This automatic generation comprises, for example, creating common name variations, creating additional clinical events and/or observations, removing clinical events and/or observations, and/or other possible slight alterations. According to testing of the training, the resulting 20-bit vectors had a slightly weaker correlation of about 2% of randomly generated files. However, in view of the extensive compression applied to generate these bit vectors, a slightly weaker correlation is an acceptable result.

Figure 3:
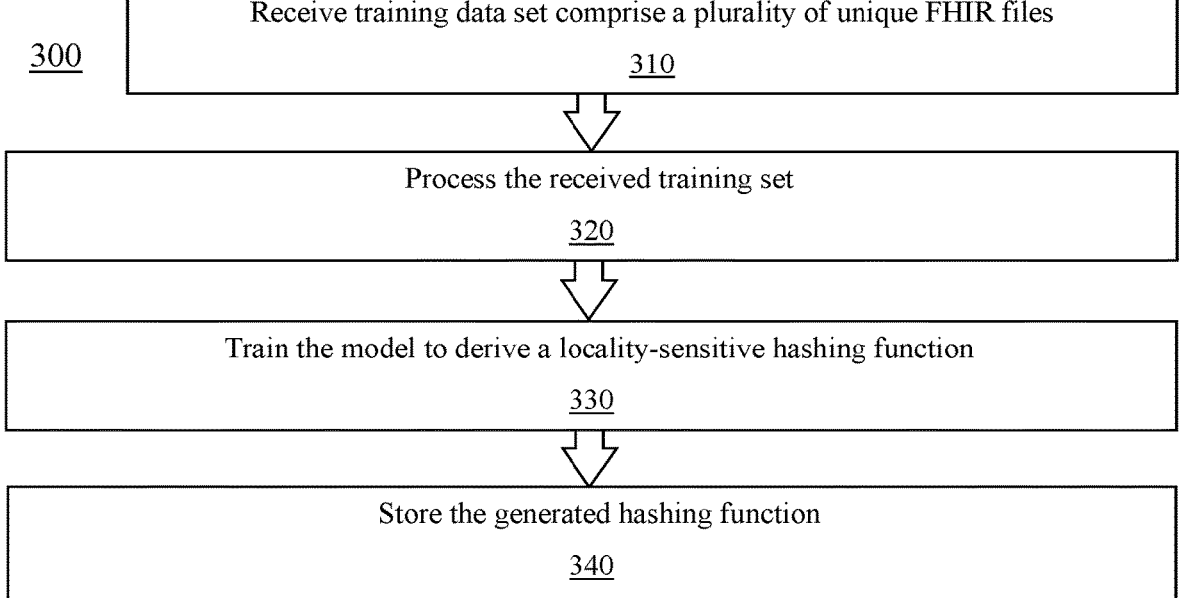
FIG. 3 is a schematic representation of a method for training a component of a FHIR file compression system, in accordance with an embodiment.

Referring to FIG. 3, in in one embodiment, is a flowchart of a method 300 for training the iterative quantization compression algorithm of the file compression system to, for example, generate the suitable special-purpose locality sensitive hashing function. At step 310 of the method, the system receives or obtains a plurality of FHIR files that will be utilized as a training dataset to train the iterative quantization compression algorithm. The FHIR files are unique such that there are no substantive similarities between the files. The FHIR files can be real or artificially generated FHIR files, and can each comprise any information about a patient. According to an embodiment, the FHIR files comprise only the information about a patient that will be utilized to train the algorithm and/or be utilized for similarity searching. According to another embodiment, the FHIR files can comprise information in addition to the information about a patient that will be utilized to train the algorithm and/or be utilized for similarity searching. This training data may be stored in and/or received from one or more databases. The database may be a local and/or remote database. For example, the file compression system may comprise a database of training data.

According to an embodiment, the file compression system may comprise a data pre-processor or similar component or algorithm configured to process the received training data. For example, the data pre-processor analyzes the training data to remove noise, bias, errors, and other potential issues.

At step 320 of the method, the FHIR files in the training dataset are processed. According to an embodiment, the files are processed by labeling similarities between files discovered by measuring the Spearman correlation to the result of algorithm three, and by automatically generating slightly altered duplicates. This automatic generation comprises, for example, creating common name variations, creating additional clinical events and/or observations, removing clinical events and/or observations, and/or other possible slight alterations. The outcome of the processing step of the file compression system is a set of FHIR files that comprise a training dataset that can be utilized to train the iterative quantization algorithm.

At step 330 of the method, the system trains the iterative quantization algorithm to generate the suitable special-purpose locality sensitive hashing function. The algorithm is trained using the training dataset according to known methods for training a machine learning algorithm. According to an embodiment, the algorithm is trained, using the processed training dataset, to create a locality-sensitive hashing function that will compress FHIR files to bit vectors of a desired length.

Following step 330 of the method, the file compression system comprises a locality-sensitive hashing function that can be utilized to compress the generated FHIR fingerprint files to a desired-length bit vector. The hashing function can be static such that it is generated once and is utilized for compression. According to another embodiment, the system can be more dynamic such that the hashing function is updated or generated anow using subsequently available training data. The updating or new generation can be constant or can be periodic.

At step 340 of the method, the generated hashing function can be stored locally or remotely for subsequent compression of generated FHIR fingerprint files.

Returning to the method depicted in FIG. 1, the file compression system has generated a fixed-length bit vector representing the FHIR fingerprint of each of a plurality of FHIR files. Accordingly, at step 112 of the method, the file compression system stores the compressed FHIR fingerprint (i.e., the generated fixed-length bit vector) in a database. The database may be a local or remote database and is a component of or otherwise in communication with the file compression system 200. According to an embodiment, the file compression system comprises a bit vector database which is optionally in direct and/or indirect communication with system 200.

At optional step 114 of the method, the file compression system or another suitable system may be utilized to search for similarities among the FHIR files by searching for similarities among the generated and stored fixed-length bit vector representing those FHIR files. Given the very small size of the stored bit vectors, searching for similarities among the files or to an input or query file is fast and efficient. The search for similar files may be accomplished using any method, system, or algorithm capable of and suitable for identifying similarities among the stored bit vectors. According to an embodiment, the similarity search may comprise a threshold or other parameter for identifying suitable similarity.

At optional step 116 of the method, the file compression system may provide a report to a user via a user interface 240 of the file compression system 200, comprising an identification of one or more FHIR files identified by the similarity search as being suitably similar to another FHIR file, and/or to an input or query file. According to an embodiment, the system may display a report on a display of the system. The display may comprise information about the FHIR file, the patient, and/or one or more parameters utilized for similarity searching. Other information is possible. Alternatively, the report may be communicated by wired and/or wireless communication to another device. For example, the system may communicate the report to a mobile phone, computer, laptop, wearable device, and/or any other device configured to allow display and/or other communication of the report.

Referring to FIG. 2 is a schematic representation of a file compression system 200. System 200 may be any of the systems described or otherwise envisioned herein, and may comprise any of the components described or otherwise envisioned herein. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, storage 260 of system 200 may store one or more algorithms, modules, and/or instructions to carry out one or more functions or steps of the methods described or otherwise envisioned herein. For example, the system may comprise, among other instructions or data, an electronic medical record system 270, training dataset 280, FHIR fingerprint instructions 262, training instructions 263, a locality-sensitive hashing function 264, similarity search instructions 265, and/or reporting instructions 266, among many other possible instructions and/or data.

According to an embodiment, the electronic medical record system 270 is an electronic medical records database from which a plurality of FHIR files may be obtained or received. The electronic medical records database may be a local or remote database and is in communication the file compression system 200. According to an embodiment, the file compression system comprises an electronic medical record database or system 270 which is optionally in direct and/or indirect communication with system 200.

According to an embodiment, the training data set 280 is a dataset may be stored in a database that may be a local or remote database and is in communication the file compression system 200. According to an embodiment, the file compression system comprises a training data set 280. The training data can comprise, for example, a plurality of FHIR files utilized to train the iterative quantization compression algorithm. The plurality of FHIR files can be unique such that there are no substantive similarities between the files. The FHIR files can be real or artificially generated FHIR files, and can each comprise any information about a patient.

According to an embodiment, FHIR fingerprint instructions 262 direct the system to generate a fixed-length FHIR patient profile fingerprint using an extracted predetermined plurality of different resource types and associated data items. According to an embodiment, the fixed-length FHIR patient profile fingerprint comprises a fixed-length floating point value feature vector. According to an embodiment, the fixed-length floating point value feature vector includes a predetermined plurality of sub-feature vectors each representing one of the predetermined and selected different extracted resource types. According to an embodiment, each sub-feature vector comprises a plurality of elements, such as the extracted associated data items, associated with the respective extracted resource type. The length of the fixed-length FHIR patient profile fingerprint can be predetermined by a user or by the system.

According to an embodiment, training instructions 263 direct the system to utilize the training dataset 280 to generate a locality-sensing hashing function 264 as described or otherwise envisioned herein. Thus, the system comprises a locality-sensing hashing function 264 that can be utilized to generate FHIR file bit vectors that can be stored in a database.

According to an embodiment, similarity search instructions 265 direct the system to search for similarities among the FHIR files by searching for similarities among the generated and stored fixed-length bit vector representing those FHIR files. The search for similar files may be accomplished using any method, system, or algorithm capable of and suitable for identifying similarities among the stored bit vectors. According to an embodiment, the similarity search may comprise a threshold or other parameter for identifying suitable similarity.

According to an embodiment, reporting instructions 266 direct the system to generate and provide a report to a user via a user interface comprising an identification of one or more FHIR files identified by the similarity search as being suitably similar to another FHIR file, and/or to an input or query file. According to an embodiment, the system may display a report on a display of the system. The display may comprise information about the FHIR file, the patient, and/or one or more parameters utilized for similarity searching. Other information is possible. Alternatively, the report may be communicated by wired and/or wireless communication to another device. For example, the system may communicate the report to a mobile phone, computer, laptop, wearable device, and/or any other device configured to allow display and/or other communication of the report.

According to an embodiment, the file compression system is configured to process many thousands or millions of datapoints in the input data or training dataset 280 used to generate the locality-sensing hashing function 264. For example, generating a suitable hashing function requires processing of millions of datapoints from the training dataset. This can require millions or billions of calculations to generate a suitable hashing function. As a result, the hashing function is novel and distinct based on the input data and parameters of the iterative quantization, and thus improves the functioning of the file compression system. Thus, generating a functional and suitable hashing function comprises a process with a volume of calculation and analysis that a human brain cannot accomplish in a lifetime, or multiple lifetimes.

In addition, the file compression system can be configured to continually receive or FHIR files from which can be created a FHIR fingerprint that is converted to a compressed bit vector stored in memory. This requires the analysis of thousands or millions of datapoints on a continual basis, requiring a volume of calculation and analysis that a human brain cannot accomplish in a lifetime. Further, by providing significantly smaller FHIR files, this novel file compression system has an enormous positive effect on similarity searching.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A computer-implemented method for generating a compressed Fast Healthcare Interoperability Resources (FHIR) file using a file compression system, comprising:

training a trained compression algorithm, comprising: (i) receiving a plurality of FHIR files; (ii) processing the received plurality of FHIR files; (iii) training the compression algorithm to generate a locality-sensitive hashing function; and (iv) storing the generated locality-sensitive hashing function;

receiving an uncompressed file, the uncompressed file configured as a FHIR file;

extracting, from the uncompressed file, a predetermined plurality of different resource types;

generating, from the extracted predetermined plurality of different resource types, a fixed-length FHIR patient profile fingerprint, wherein the fixed-length FHIR patient profile fingerprint comprises a fixed-length floating point value feature vector, the fixed-length floating point value feature vector comprising a predetermined plurality of sub-feature vectors each representing a different extracted resource type, and wherein each sub-feature vector comprises a plurality of elements of the respective extracted resource type;

compressing, using the trained compression algorithm, the generated fixed-length FHIR patient profile fingerprint to generate a compressed FHIR fingerprint; and storing the compressed FHIR fingerprint in a database.

2. The method of claim 1, wherein the fixed-length floating point value feature vector comprises six sub-feature vectors.

3. The method of claim 1, wherein the compressed FHIR fingerprint comprises a fixed-length bit vector.

4. The method of claim 3, wherein the trained compression algorithm comprises an iterative quantization approach.

5. The method of claim 4, wherein the iterative quantization approach generates a locality-sensitive hashing function configured to generate the fixed-length bit vector from the generated fixed-length FHIR patient profile fingerprint.

6. The method of claim 1, wherein processing the received plurality of FHIR files comprises: (i) labeling one or more similarities between the received plurality of FHIR files; and/or (ii) altering one or more of the received plurality of FHIR files to generate an altered FHIR file.

7. The method of claim 1, further comprising the step of searching for similarity to one or more of the compressed FHIR fingerprints stored in the database.

8. The method of claim 7, further comprising the step of reporting a result of the step of searching for similarity to one or more of the compressed FHIR fingerprints stored in the database.

9. A system for generating a compressed Fast Healthcare Interoperability Resources (FHIR) file, comprising:

an electronic medical record database comprising a plurality of uncompressed files, each of the uncompressed files configured as a FHIR file;

a locality-sensitive hashing function configured to generate a fixed-length bit vector from a generated fixed-length FHIR patient profile fingerprint; and a processor configured to generate the locality-sensitive hashing function by: (i) receiving a plurality of FHIR files; (ii) processing the received plurality of FHIR files; (iii) training a compression algorithm to generate the locality-sensitive hashing function; and (iv) storing the generated locality-sensitive hashing function; the processor is further configured to: (i) extract, from each of the plurality of uncompressed files, a predetermined plurality of different resource types; (ii) generate, from the extracted predetermined plurality of different resource types, a fixed-length FHIR patient profile fingerprint, wherein the fixed-length FHIR patient profile fingerprint comprises a fixed-length floating point value feature vector, the fixed-length floating point value feature vector comprising a predetermined plurality of sub-feature vectors each representing a different extracted resource type, and wherein each sub-feature vector comprises a plurality of elements of the respective extracted resource type; (iii) compress, using the locality-sensitive hashing function, the generated fixed-length FHIR patient profile fingerprint to generate a compressed FHIR fingerprint; and (iv) store the compressed FHIR fingerprint in a database.

10. The system of claim 9, wherein the compressed FHIR fingerprint comprises a fixed-length bit vector.

11. The system of claim 9, wherein processing the received plurality of FHIR files comprises: (i) labeling one or more similarities between the received plurality of FHIR files; and/or (ii) altering one or more of the received plurality of FHIR files to generate an altered FHIR file.

12. The system of claim 9, wherein the processor is further configured to search for similarity to one or more of the compressed FHIR fingerprints stored in the database.

13. The system of claim 12, wherein the system further comprises a user interface, and the processor is further configured to report, via the user interface, a result of searching for similarity to one or more of the compressed FHIR fingerprints stored in the database.

* * * * *